(12) United States Patent
Francis et al.

(10) Patent No.: US 8,838,216 B2
(45) Date of Patent: Sep. 16, 2014

(54) METHOD OF AND APPARATUS FOR GENERATING A MODEL OF A CARDIAC SURFACE HAVING A PLURALITY OF IMAGES REPRESENTING ELECTROGRAM VOLTAGES

(75) Inventors: Darrel Parthipan Francis, Harrow (GB); Prapakaran Kanagaratnam, London (GB); Nicholas William Fox Linton, London (GB)

(73) Assignee: Imperial Innovations Limited, London (GB)

(*) Notice: Subject to any disclaimer, the term of this patent is extended or adjusted under 35 U.S.C. 154(b) by 1031 days.

(21) Appl. No.: 12/598,886

(22) PCT Filed: May 2, 2008

(86) PCT No.: PCT/GB2008/001521
§ 371 (c)(1),
(2), (4) Date: Jun. 25, 2010

(87) PCT Pub. No.: WO2008/135731
PCT Pub. Date: Nov. 13, 2008

(65) Prior Publication Data
US 2010/0280399 A1    Nov. 4, 2010

(30) Foreign Application Priority Data
May 4, 2007   (GB) ................... 0708781.0

(51) Int. Cl.
| A61B 5/04 | (2006.01) |
| G06F 19/00 | (2011.01) |
| G06T 17/20 | (2006.01) |
| A61B 6/00 | (2006.01) |
| A61B 5/042 | (2006.01) |

(52) U.S. Cl.
CPC ........ *A61B 5/04011* (2013.01); *G06F 19/3437* (2013.01); *G06T 17/20* (2013.01); *A61B 6/503* (2013.01); *A61B 5/0422* (2013.01)
USPC .......................................................... 600/509

(58) Field of Classification Search
USPC ................................................. 600/508–509
See application file for complete search history.

(56) References Cited

U.S. PATENT DOCUMENTS 5,151,856 A * 9/1992 Halmann et al. .............. 600/508
5,687,737 A 11/1997 Branham et al.
(Continued)

FOREIGN PATENT DOCUMENTS

| EP | 1070480 A | 1/2001 |
| EP | 1779787 A2 | 5/2007 |

OTHER PUBLICATIONS

International Search Report for PCT/GB2008/001521 dated Oct. 1, 2008.

*Primary Examiner* — Christopher D Koharski
*Assistant Examiner* — Elizabeth K So
(74) *Attorney, Agent, or Firm* — Heslin Rothenberg Farley & Mesiti P.C.

(57) ABSTRACT

A method of generating a model of a cardiac surface having a plurality of images representing electrogram voltages for a plurality of measured points within a heart comprises measuring an electrogram voltage at a plurality of points within a heart, generating a first model of a cardiac surface of the heart, generating an image representing each electrogram voltage, each image having a characteristic representative of the electrogram voltage, and generating a further model of a cardiac surface. The images representing the electrogram voltages protrude from the further model of the cardiac surface at points on the further model corresponding to the points at which the electrogram voltages were measured. There is also disclosed an apparatus for generating a model of a cardiac surface.

40 Claims, 9 Drawing Sheets

(56) References Cited

U.S. PATENT DOCUMENTS

| | | | |
|---|---|---|---|
| 5,871,019 A * | 2/1999 | Belohlavek | 600/450 |
| 6,950,689 B1 | 9/2005 | Willis et al. | |
| 2003/0231789 A1 | 12/2003 | Willis et al. | |
| 2004/0082870 A1 | 4/2004 | Rudy et al. | |
| 2005/0209525 A1 | 9/2005 | Bojovic et al. | |
| 2007/0073179 A1 | 3/2007 | Afonso et al. | |

* cited by examiner

METHOD OF AND APPARATUS FOR GENERATING A MODEL OF A CARDIAC SURFACE HAVING A PLURALITY OF IMAGES REPRESENTING ELECTROGRAM VOLTAGES

CROSS REFERENCE TO RELATED APPLICATIONS

This application is a national stage filing under section 371 of International Application No. PCT/GB2008/001521 filed on May 2, 2008, and published on Nov. 13, 2008 as WO 2008/135731 and claims priority of Great Britain application No. 0708781.0 filed on May 4, 2007, the entire disclosure of these applications being hereby incorporated herein by reference.

FIELD OF THE INVENTION

The present invention relates to a method of and apparatus for generating a model of a cardiac surface having a plurality of images representing electrogram voltages.

BACKGROUND OF THE INVENTION

Individuals with irregular heart beats (arrhythmias) may need to undergo procedures to treat the heart by local intervention. Some individuals may have disabling symptoms as well as being at risk of death from their arrhythmia. During conventional procedures, a doctor will attempt to identify the pattern of electrical propagation through the walls of the heart. This is typically achieved by touching a catheter to the internal surface of the heart and recording the voltage (electrogram) at multiple positions. After an electrical 'map' has been constructed, ablation is typically performed by delivering radiofrequency energy to selected locations in order to create scar tissue. This scar tissue alters electrical propagation through the myocardium, hopefully treating the arrhythmia.

One of the most difficult aspects of these procedures is selecting the correct locations for ablation. The reason for this is that the surface of the heart is a complex three-dimensional structure which is traversed, during the procedure, with a probing catheter that can only record the electrogram at one position at a time.

A number of conventional techniques exist for constructing an electrical map of a heart, such as Isochronal Activation Mapping and Isopotential Mapping.

The technique of Isochronal Activation Mapping is as follows. In order to stimulate heart muscle to contract, an electrical signal travels through the myocardium like a wave. Points on a displayed image of an individual's heart are coloured according to the time when electrical activation occurs. Therefore, points that have 'isochronal activation' (that is, points which activate at the same time) will be displayed as having the same colour. There are a number of problems with this conventional technique including:

- The catheter measures electrical activity within a small region of myocardium near its tip. However, often, there will be more than one activation time if different parts of myocardium in this region activate at different times or myocardial activation is abnormal in character and, using conventional Isochronal Activation Mapping, this complex electrical activation pattern may have to be represented at a single time point (the activation time) and there may therefore be a significant loss of information about the quality of the local activation pattern (in terms of amplitude, duration and degree of fractionation).

Errors occur in detecting the position of the electrode relative to the heart. This means that the 3D visualization of the collection of sample points is difficult. Visualization is currently aided by the display of an interpolated surface that links the sampled points. However, this can be misleading if there is a large distance between neighbouring samples. Conventional methods do not show all of the sampled points on the same surface.

Due to the above problems, an experienced member of staff is required to assist with data manipulation before the data may be displayed.

In the conventional technique of Isopotential Mapping, the surface of the heart is displayed and coloured according to the electrogram voltage. Hence, areas with the same voltage (isopotential) have the same colour. The colour varies as the voltage changes with time. A conventional 'true' isopotential mapping system is the EnSite System™ of St Jude Medical. This system reconstructs the endocardial surface electrogram using inverse solutions from a far-field electrogram recorded from a non-contact intra-cardiac electrode. Conventional Isopotential Mapping has the benefit of not needing the activation time to be marked by a technician with electrophysiology experience. However, Isopotential mapping has a number of problems such as:

- 'Retraining' the eye to interpret the colour-scales is difficult and requires a lot of practice.
- All the data points are extrapolated, and not directly acquired, and therefore are susceptible to distance error and other artefact.
- This technology cannot be directly applied to data obtained from a catheter that obtains electrograms at individual points. It is applicable when the voltage across the entire surfaces of myocardium is known.

Thus there is a need for an improved system and method for recording, integrating and displaying this information which enables the time taken to perform these procedures to be reduced, enables the success rate of the procedures to be improved and patient safety to be increased by improved selection of ablation locations.

SUMMARY OF THE INVENTION

According to a first aspect of the present invention there is provided a method of generating a model of a cardiac surface having a plurality of images representing electrogram voltages for a plurality of measured points within a heart comprising:

internally measuring an electrogram voltage at a plurality of points within a heart; generating a first model of a cardiac surface of said heart;

generating an image representing each electrogram voltage, each image having a characteristic representative of the electrogram voltage; and generating a further model of a cardiac surface, said images representing said electrogram voltages protruding from said further model of said cardiac surface at points on said further model corresponding to the points at which said electrogram voltages were measured.

In a preferred embodiment, the step of generating the first model of said cardiac surface comprises:

(a) obtaining three-dimensional coordinates of the locations of said plurality of points at which said electrogram voltages were measured;

(b) fitting a surface of a three-dimensional representation of a solid to said three-dimensional coordinates;
(c) locating on the surface of said solid a plurality of points, one or more of said points corresponding to a respective one of said plurality of points at which said electrogram voltages were measured to generate associated surface points on said representation of said solid;
(d) dividing said surface of said representation of said solid into a plurality of triangles, each triangle having an associated apex at which one of said plurality of said surface points is located;
(e) transforming the surface of said three-dimensional representation of a solid into a two-dimensional plane around a first selected triangle of said plurality of triangles using a predetermined transformation process;
(f) transforming the three-dimensional coordinates of the locations of the plurality of points at which said electrogram voltages were measured using said transformation process applied in step (e) to said surface;
(g) connecting a number of said transformed points at which said electrogram voltages were measured to other of said transformed points at which said electrogram voltages were measured to form a further surface using an interpolation method;
(h) sampling an interpolated area within said first selected triangle, that was interpolated using the bicubic spline interpolation method, the samples being adjusted with a weighted average to obtain a shape representative of the surface of said triangle;
(i) repeating steps (e), (f), (g) and (h) for each triangle of said plurality of triangles to obtain a plurality of three-dimensional surfaces representative of each of said plurality of triangles; and
(j) transforming the three-dimensional surfaces into a three-dimensional model to form the first model of said cardiac surface.

Preferably, in step (g), the interpolation method used is a bicubic spline interpolation method.

Preferably, the step of measuring an electrogram voltage at a plurality of points within a heart comprises measuring a maximum voltage for said plurality of said points and performing one or more of the steps (a) to (j) using said measured maximum voltage.

In a preferred embodiment, the step of generating an image representing each electrogram voltage comprises generating a bar. One or more of said bars may have a length representative of the measured electrogram voltage.

Furthermore, one or more of said bars may extend in a plane substantially perpendicular to said further model at the points of connection thereto. This is advantageous as it results in neighbouring electrograms being slightly divergent thereby inhibiting collisions between neighbouring electrograms.

Preferably, the method further comprises transforming the length of one or more of said bars to enhance visibility of small disturbances from baseline. In a preferred embodiment, the step of transforming the length of one or more of said bars to enhance visibility of small disturbances from baseline comprises transforming using one or more of a series of transformations having one or more characteristics adjustable by a user.

Preferably, said further model of said cardiac surface is movable; for example, said further model of said cardiac surface may be rotatable and able to be manipulated in three-dimensions to optimize the view of interesting areas. This may be achieved may be controlled by a graphical user interface control.

In a preferred embodiment, said electrogram voltages are measured at a predetermined time in a cardiac cycle, the method further comprising varying the predetermined time within the cardiac cycle to obtain a revised representation on the further model at one or more further predetermined times within the cardiac cycle of the images representing each electrogram voltage at said one or more further predetermined times.

In a further preferred embodiment, one or more colours may be applied to said surface to assist the user.

Preferably, the step of fitting a three-dimensional representation of a solid comprises fitting the three-dimensional representation of said solid having a continuous surface to said measured points. The display of a continuous surface is helpful to assist the user in visualizing the 'electrogram bars' but is not obligatory.

Preferably, the step of fitting a solid comprises fitting one or other of a sphere or an ellipsoid to said three-dimensional coordinates.

Preferably, the method further comprises altering one or more of a viewing angle of said further model, magnification of said further model, and/or the time at which the electrograms are displayed within a cardiac cycle.

Preferably, the first model has a surface, and the method further comprises smoothing the cardiac surface of the first model according to one or more user preferences.

Preferably, the method further comprises generating a movie of the images representing of the images representing the electrogram voltages on the further model by displaying the images of electrogram voltages measured at various predetermined times during a cardiac cycle.

In a preferred embodiment, the step of generating the first model of said cardiac surface comprises:
generating said first model using a reconstructed three-dimensional computed tomography (3D CT) process.
In an alternative preferred embodiment, the step of generating the first model of said cardiac surface comprises:
generating said first model using a reconstructed rotational angiography process.

According to a second aspect of the present invention there is provided an apparatus for generating a model of a cardiac surface having a plurality of images representing electrogram voltages for a plurality of measured points within a heart comprising:
a first stage arranged to internally measure an electrogram voltage at a plurality of points within a heart;
a second stage arranged to generate a first model of a cardiac surface of said heart;
a third stage arranged to generate an image representing each electrogram voltage, each image having a characteristic representative of the electrogram voltage; and
a fourth stage arranged to generate a further model of a cardiac surface, said images representing said electrogram voltages protruding from said further model of said cardiac surface at points on said further model corresponding to the points at which said electrogram voltages were measured.

Preferably, the second stage comprises:
(a) a three-dimensional coordinate determination stage to determine the three-dimensional coordinates of the locations of said plurality of points at which said electrogram voltages were measured;
(b) a fitting stage to fit a surface of a three-dimensional representation of a solid to said three-dimensional coordinates;
(c) a location stage to locate on the surface of said solid a plurality of points, one or more of said points corresponding to a respective one of said plurality of points at which said electrogram voltages were measured to generate associated surface points on said representation of said solid;

(d) a divider stage to divide said surface of said representation of said solid into a plurality of triangles, each triangle having an associated apex at which one of said plurality of said surface points is located;

(e) a first transformation stage arranged to transform the surface of said three-dimensional representation of a solid into a two-dimensional plane around a first selected triangle of said plurality of triangles using a predetermined transformation process;

(f) a second transformation stage arranged to transform the three-dimensional coordinates of the locations of the plurality of points at which said electrogram voltages were measured using said transformation process applied to said surface;

(g) a connecting stage to connect a number of said transformed points at which said electrogram voltages were measured to other of said transformed points at which said electrogram voltages were measured to form a further surface using an interpolation method;

(h) a sampling stage to sample an interpolated area within said first selected trianglethat was interpolated using the bicuic spline interpolation method, the samples being adjusted with a weighted average to a shape representative of the surface of said triangle;

(i) said first and second transformation stages, said connecting stage and said sampling stage being arranged to operate on each triangle of said plurality of triangles to obtain a plurality of three-dimensional surfaces representative of each of said plurality of triangles; and (j) a third transformation stage arranged to transform the three-dimensional surfaces into a three-dimensional model to form the first model of said cardiac surface.

Preferably, said first stage is arranged to measure a maximum electrogram voltage for said plurality of said points, wherein one or more of said three-dimensional coordinate determination stage, said fitting stage, said location stage, said divider stage, said first transformation stage, said second transformation stage, said connecting stage, and said sampling stage being arranged to operate using said measured maximum voltage.

In a preferred embodiment, said image representing each electrogram voltage comprises a bar, wherein one or more of said bars may have a length representative of the measured electrogram voltage. Further, one or more of said bars may extend in a plane substantially perpendicular to said further model at the paints of connection thereto.

In a further preferred embodiment, the apparatus further comprises a transformation stage arranged to transform the length of one or more of said bars to enhance visibility of small disturbances from baseline. Preferably, the transformation stage is arranged to transform the length of one or more of said bars to enhance visibility of small disturbances from baseline by one or more of a series of transformations having one or more characteristics adjustable by a user.

In a preferred embodiment, said further model of said cardiac surface is movable and may, for example, be rotatable.

Preferably, said electrogram voltages are measured at a predetermined time in a cardiac cycle, the apparatus further comprising varying the predetermined time within the cardiac cycle to obtain a revised representation on the further model at one or more further predetermined times within the cardiac cycle of the images representing each electrogram voltage at said one or more further predetermined times.

Preferably, said surface has one or more colours applied to said surface.

In a preferred embodiment, said fitting stage is arranged to fit the three-dimensional representation of said solid having a continuous surface to said measured points. Preferably, the fitting stage is arranged to fit one or other of a sphere or an ellipsoid to said three-dimensional coordinates.

Preferably, said apparatus further comprises a stage for altering one or more of a viewing angle of said further model, magnification of said further model, and/or the time at which the electrograms are displayed within a cardiac cycle.

In a preferred embodiment, said apparatus further comprises a stage arranged to generate a moving representation of the images representing the electrogram voltages on the further model by displaying the images of electrogram voltages measured at various predetermined times during a cardiac cycle.

In a further preferred embodiment, the second stage is arranged to generate the first model of said cardiac surface using a reconstructed three-dimensional computed tomography (3D CT) process.

In an alternative further preferred embodiment, the second stage is arranged to generate the first model of said cardiac surface using a reconstructed rotational angiography process.

BRIEF DESCRIPTION OF THE DRAWINGS

The present invention will now be described by way of example and with reference to the accompanying drawings in which.

DETAILED DESCRIPTION OF PREFERRED EMBODIMENTS

Preferred embodiments of the present innovation permit the user to visualize changing electrogram voltages across a 3D surface such as the surface an individual's heart and permit the simultaneous display of the variation of the electrogram with time at each measurement point, to improve visualisation of cardiac activation patterns.

The process embodying the present invention preferably comprises two main stages, firstly drawing the surface of the heart under consideration and then displaying the electrograms associated with that surface.

Initially, raw data comprising a number of recordings from an intra-cardiac catheter, is acquired using standard conventional clinical methods. Each recording consists of the position of the catheter relative to the individual whose heart is under consideration (in 3D), a surface ECG recorded from skin electrodes and an electrogram recorded from the intra-cardiac catheter.

Figure 1:
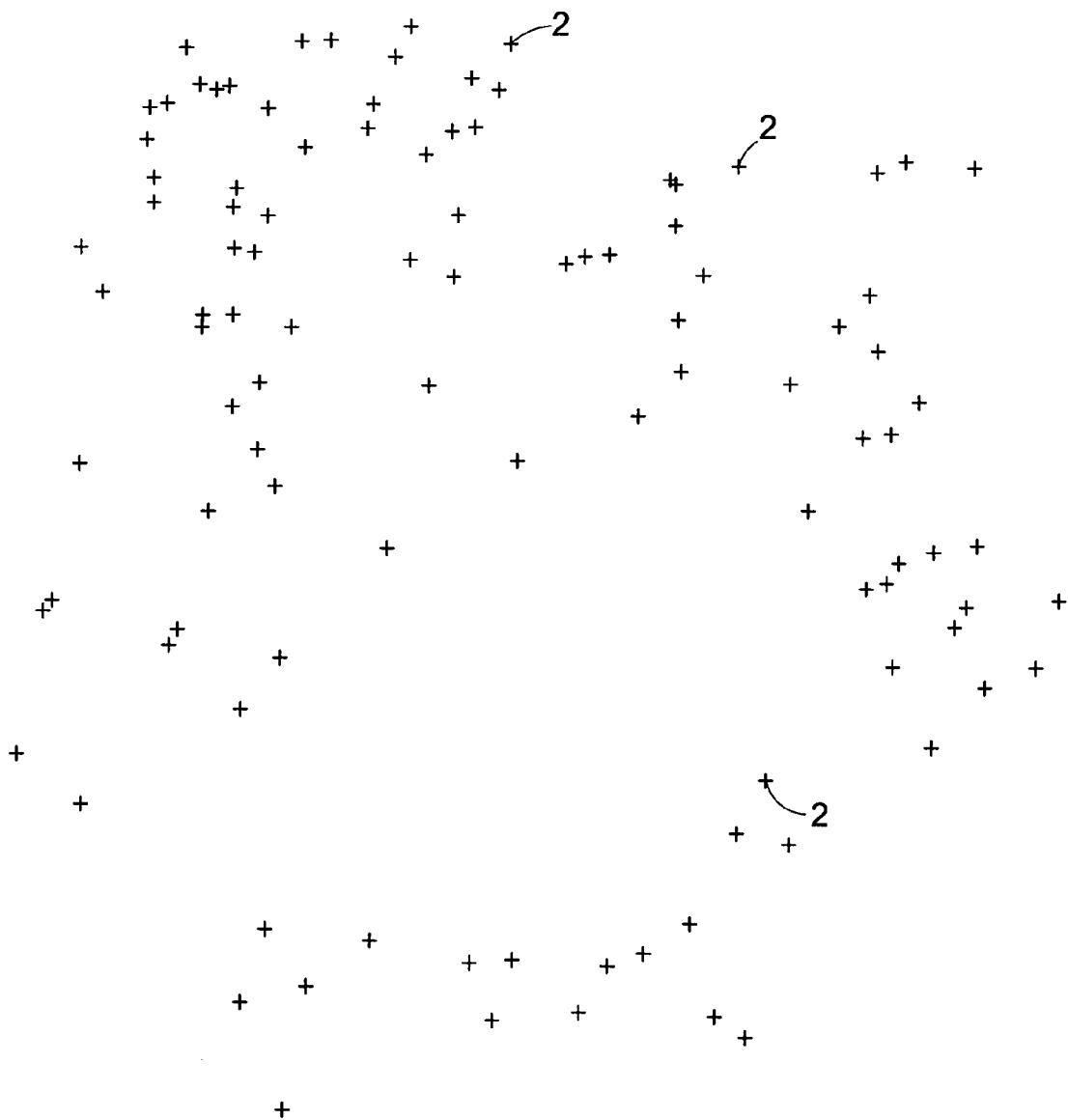
FIG. 1 is a graphical representation illustrating the 3D locations of positions where electrical measurements of points on a heart's surface have been taken.

As shown in FIG. 1, in a first stage, the measured points 2 of the position of the catheter are recorded. The 3D co-ordinates of each measured point 2 may be imported from standard conventional clinical catheter location technology, for example, CARTO, LOCAL1SA, NAV-X. The original 3D measured points 2 form an uneven surface, in part due to motion of the individual's heart under consideration. Thus, the original position measurements are subject to measurement error mainly because the heart moves within the patient's chest during the cardiac and respiratory cycles. The measurement of the catheter position is made relative to the position of the individual under consideration and not relative to the individual's heart. To reduce the spatial errors, a series of steps are performed as described below.

Figure 2:
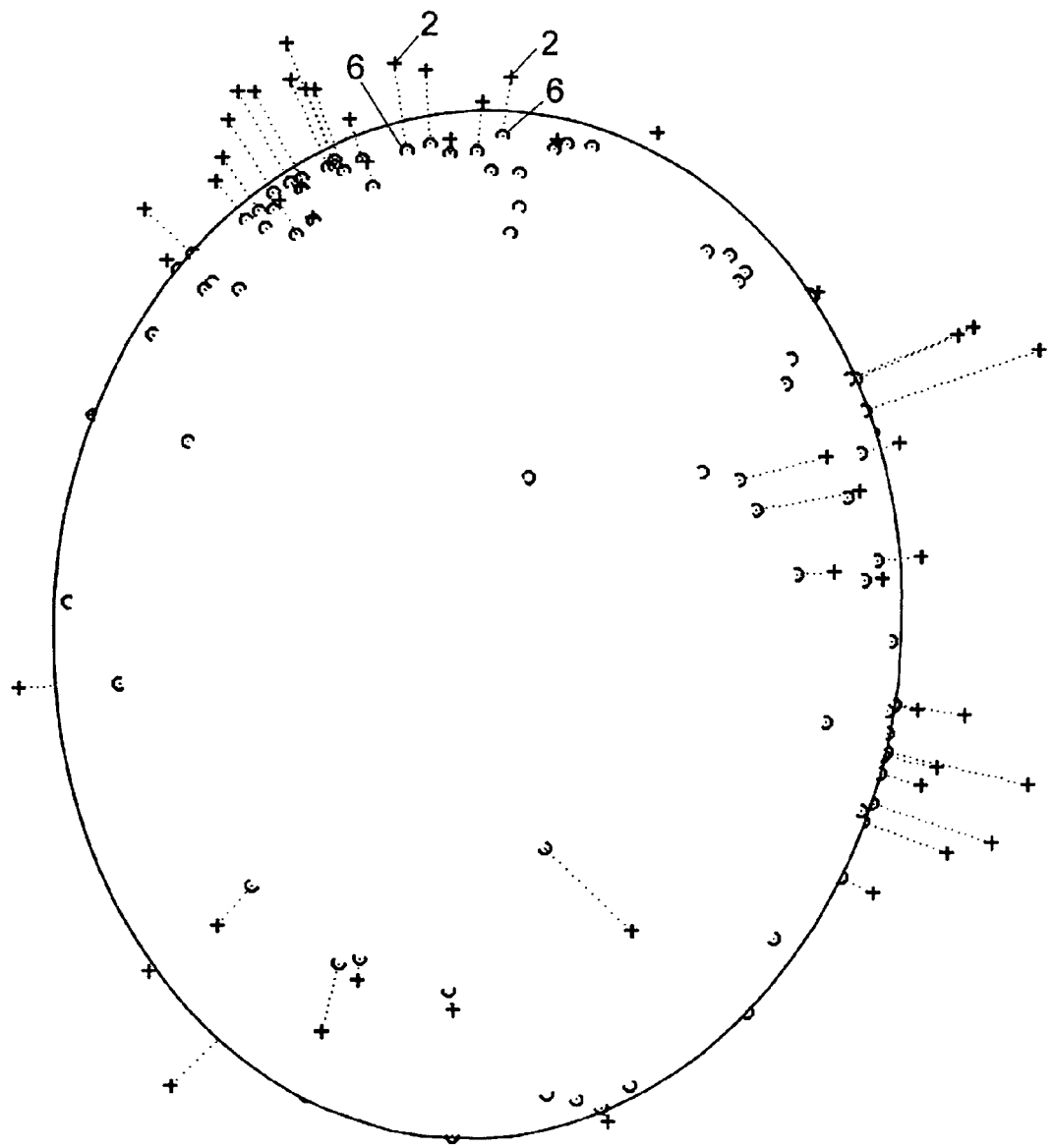
FIG. 2 is a graphical representation of a convex solid fitted, in accordance with a preferred embodiment of the present invention, to the points illustrated in FIG. 1 with the nearest points on surface of the ellipsoid (hereinafter referred to as surface points) to the actual location points also shown.

In a second stage, as shown in FIG. 2, the way in which the 3D measured points 2 are linked is determined by 'fitting' the points to a convex solid 4, such as an ellipsoid. In an alternative preferred method the points may be fitted to a differently shaped solid such as a sphere. The shape of the solid is preferably chosen to be a good representation for the cardiac chamber under consideration. The fitting of the measured points 2 may be achieved using an iterative least squares method (for example as set out below). The locations 6 on the ellipsoid 4 that are closest to the measured points 2 are then identified.

The distance of each point from the ellipsoid 4 may be determined by formulating a Lagrange multiplier problem, for example as follows:

Firstly the data and the ellipse are translated and rotated so that the ellipse lies with its centre on the origin and its hemi-axes aligned with the Cartesian coordinate system. Then, the equation of the ellipse may be denoted by:

$$\frac{x^2}{a^2} + \frac{y^2}{b^2} + \frac{z^2}{c^2} = 1 \qquad \text{equation 1}$$

where a, b, and c are the lengths of the three semi-axes.

At any point, a vector normal to the ellipsoid surface may be denoted by:

$$\begin{bmatrix} \frac{x}{a^2} \\ \frac{y}{b^2} \\ \frac{z}{c^2} \end{bmatrix} \qquad \text{equation 2}$$

Therefore, for a point p (that is not on the ellipse), the closest point on the ellipse will satisfy:

$$\begin{bmatrix} x \\ y \\ z \end{bmatrix} + \lambda \begin{bmatrix} \frac{x}{a^2} \\ \frac{y}{b^2} \\ \frac{z}{c^2} \end{bmatrix} = \begin{bmatrix} p_x \\ p_y \\ p_z \end{bmatrix} \qquad \text{equation 3}$$

Combining equation 1 with equation 3 gives:

$$\left(\frac{ap_x}{a^2+\lambda}\right)^2 + \left(\frac{bp_y}{b^2+\lambda}\right)^2 + \left(\frac{cp_z}{c^2+\lambda}\right)^2 = 1 \qquad \text{equation 4}$$

This cannot be solved analytically and iteration must be used to solve for $\lambda$. There are six possible solutions but the value of $\lambda$ that is positive is the value required. The location on the ellipsoid 4 may then be calculated by substituting $\lambda$ back into equation 3.

Using this scheme, the distances of each point from the ellipsoid 4 may be calculated. The centre, rotation, and semi-axes of the ellipse may then be altered iteratively to find the 'least-squares' fit ellipsoid 4.

Figure 3:
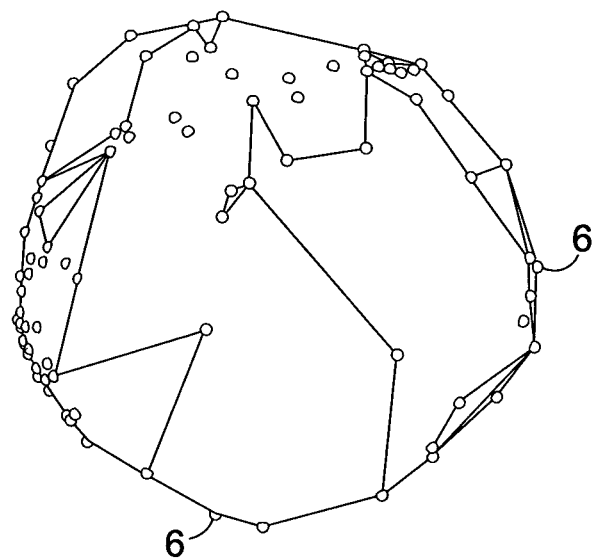
FIG. 3 is a graphical representation showing the effect of applying a series of algorithms to points on the surface nearest to the actual measurement points to obtain a series of triangles with one of said surface points at each vertex to generate a convex surface, in accordance with a preferred embodiment of the present invention.
Figure 5:
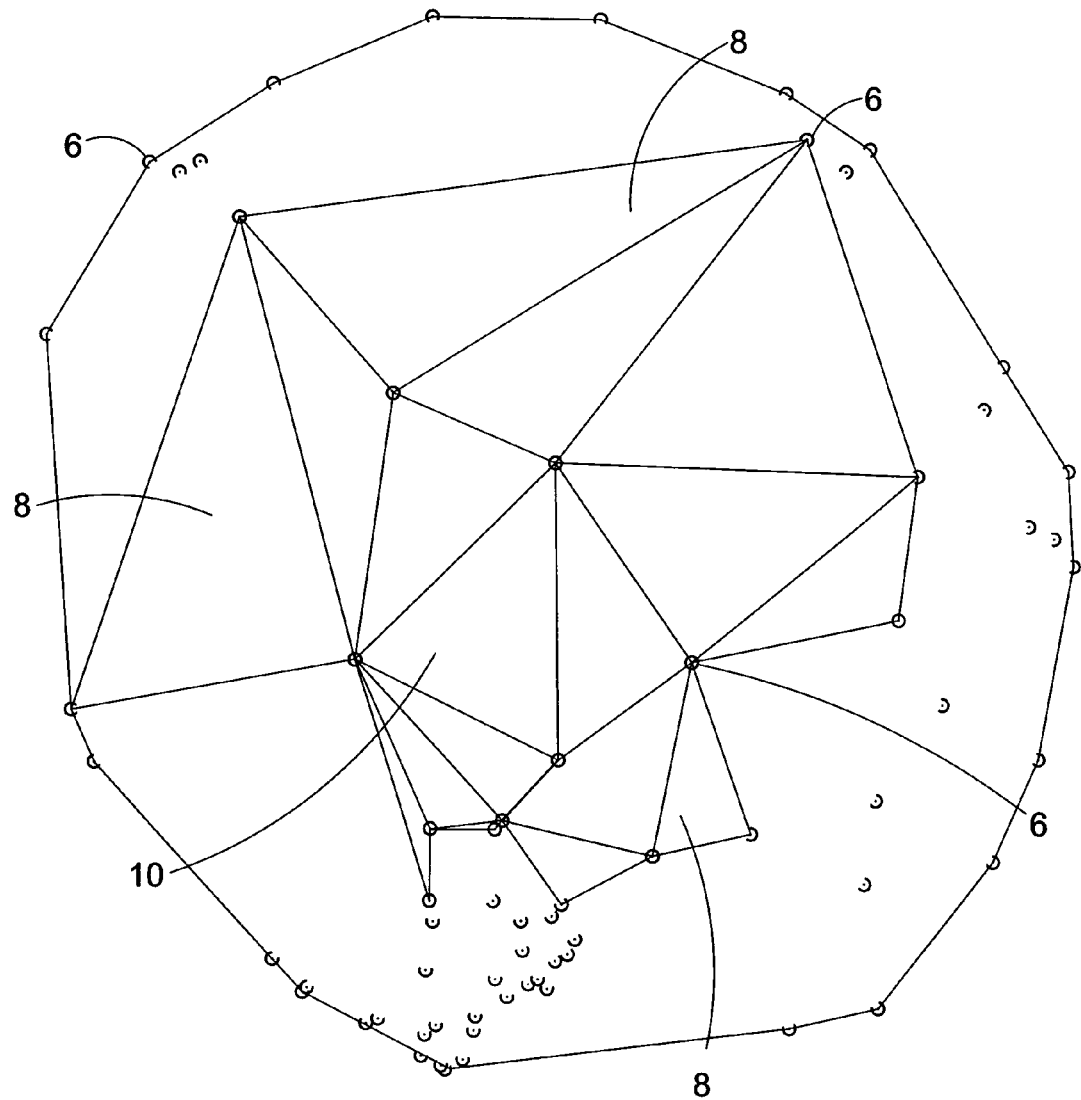
FIG. 5 shows the convex surface of FIG. 3 with the triangle to be considered for processing according to a preferred embodiment of the present invention, highlighted for reference.

FIG. 3 shows the fitted points and the locations 6 on the ellipsoid 4 that are closest to the measured points 2 as lying on the surface of the convex ellipsoid 4. These points 6, referred to hereafter as surface points, form a convex hull. Applying any one of a series of conventional convex hull algorithms, a series of triangles 8 with a surface point 6 at each vertex is obtained to connect together the surface points. The triangles 8 create a convex surface as shown in FIG. 5.

Figure 4:
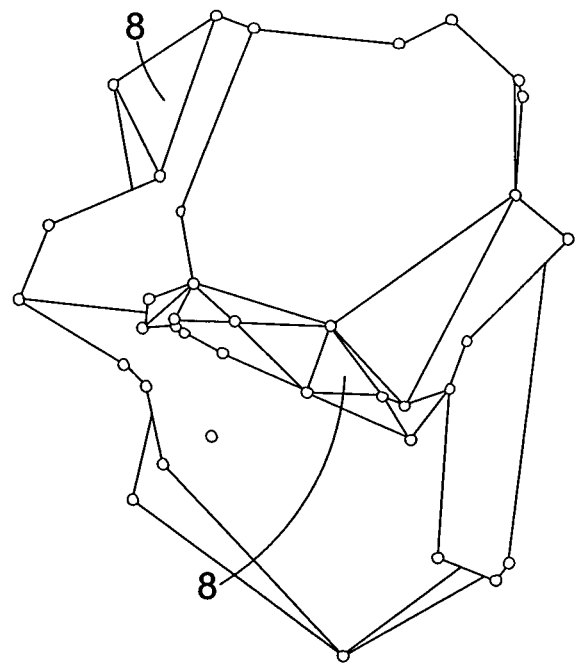
FIG. 4 is a graphical representation showing, for comparison purposes, the effect of applying the series of algorithms to measured points on the surface of the solid of FIG. 2 to obtain a series of triangles.

For the purposes of illustrative comparison, FIG. 4 shows the results of what would have been obtained if the original measured points 2 of FIG. 1 were directly tesselated rather than the surface points 6, using the same triangulation method as that applied in connection with FIG. 3. It will be seen from FIG. 4 that such an approach would not produce a smooth surface, and would make comparison of electrograms difficult.

Thus, to facilitate electrogram visualization, the surface is smoothed by modifying the distance from the convex hull 4 using the weighted average of the respective distances for other points in the vicinity. The amount of spatial smoothing may be adjusted or turned off by the user as required. This assumes that position measurements within the same locality should have a constant distance from the convex hull described above.

In order to create a smooth surface, each triangle 8 is processed in turn. For ease of understanding, FIGS. 6 to 9 relate to a first triangle 10. The process is then repeated for each triangle in turn.

Figure 6:
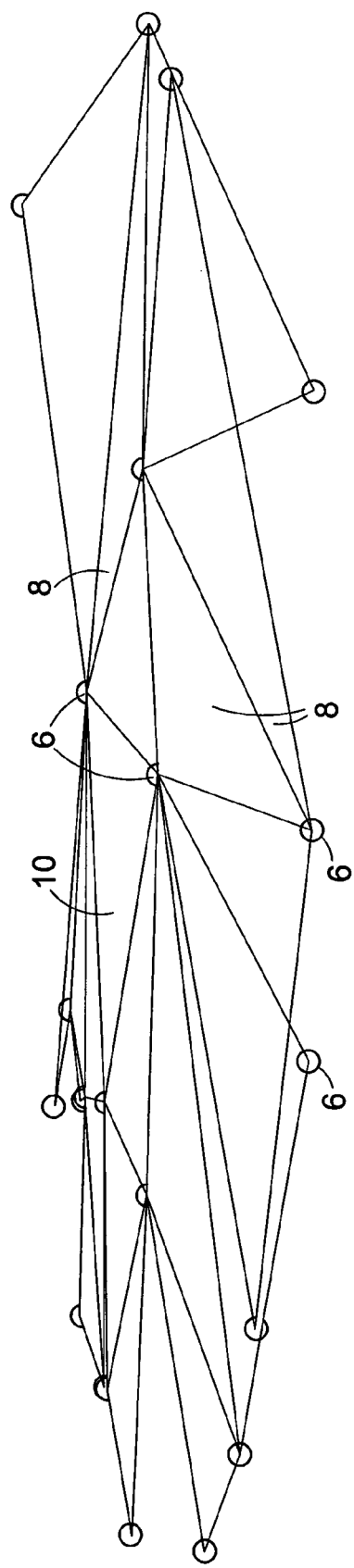
FIG. 6 is a graphical representation of the triangle of interest and adjacent triangles of FIG. 5 laid into a plane.
Figure 7:
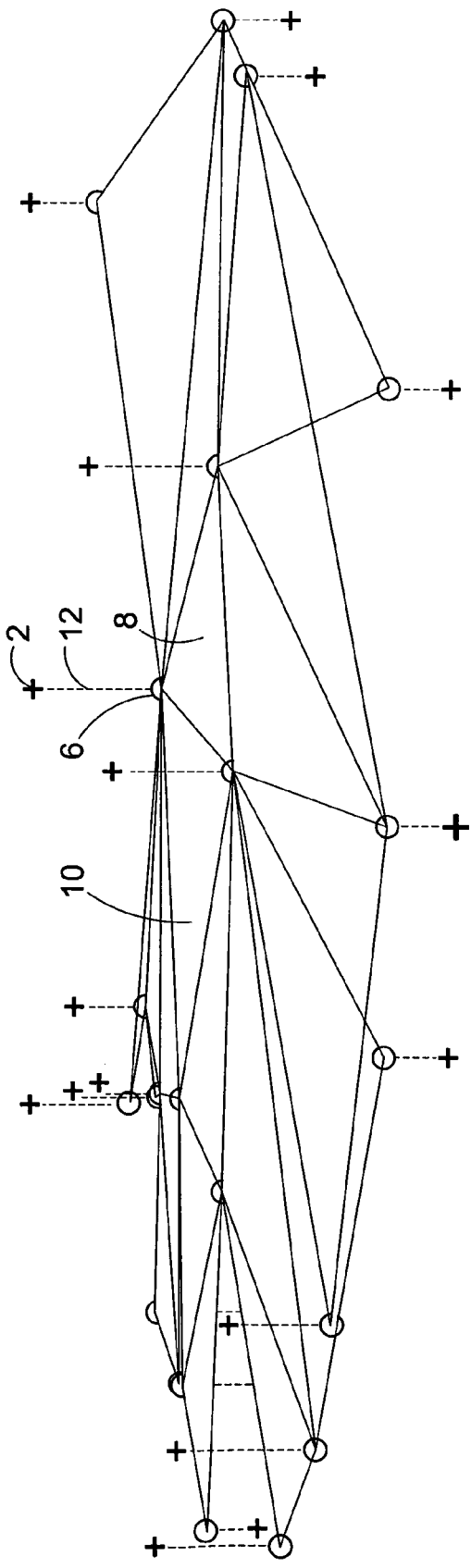
FIG. 7 is a graphical representation of the plane of triangles of FIG. 6 with the measured points attached to the corresponding surface points.

In a third stage, as shown in FIG. 6, the convex hull with the surface points 6 is 'unwrapped' into two dimensions and onto a plane around the triangle 10 of points 2 interest. In a fourth stage, as shown in FIG. 7, the original measured are unwrapped using the same transformation as applied to the surface points 6. The distances from the ellipsoid 4 to the original measured points 2, as shown in FIG. 2, are represented in FIG. 7 by the lines 12 connecting the measured points 2 to the surface points 6.

The distance between the measured points 2 and the surface points 6 is known at each location but to reduce the local variability of these distances, a smoothing operation may be performed as follows:

$$newd_i = \frac{\sum w_{ij} d_j}{\sum w_{ij}}, \quad w_{ij} = e^{\frac{-\Delta_{ij}^2}{\sigma^2}}$$

where, newd is the new distance of measured point "i" from surface point "i"

d is the original distance of measured point "j" from surface point "j"

$w_{ij}$ is a weighting factor, as defined above $\Delta_{ij}$ is the distance between surface point "i" and surface point "j"

σ is the smoothing factor

Optionally, the distances from the ellipse to the measured points 2 may be modified at this stage. For example, the distance may be replaced with a weighted average of the other distances in the vicinity. This will result in a final shape that may have smoother angles of curvature.

Figure 8:
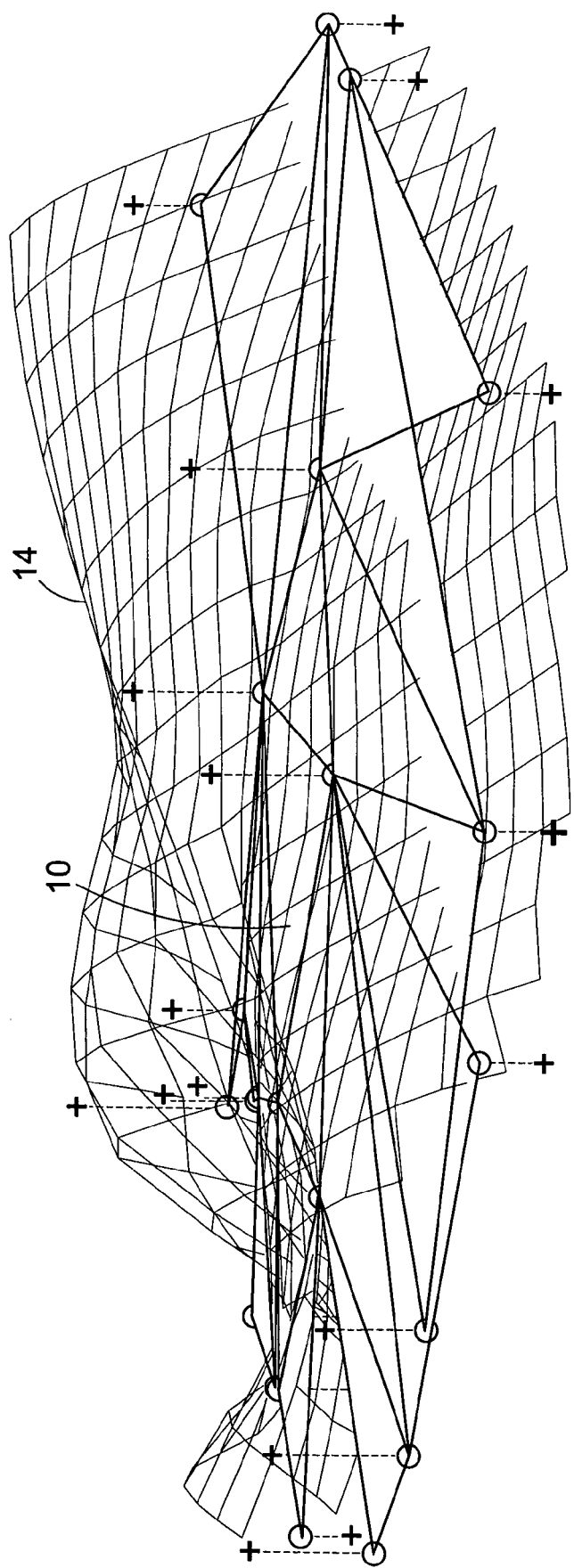
FIG. 8 is a graphical representation of the plane of triangles of FIG. 7 to which a bicubic spline interpolation has been applied to the measured points to connect the measured points in accordance with a preferred embodiment of the present invention.

In a fourth stage, as shown in FIG. 8, the distances from each point to the convex hull are then interpolated onto a fine grid using bicubic spline interpolation. These distances may then be used to 'fill in' the triangle 10 under consideration with further points that may be connected to form a smooth surface.

Figure 9:
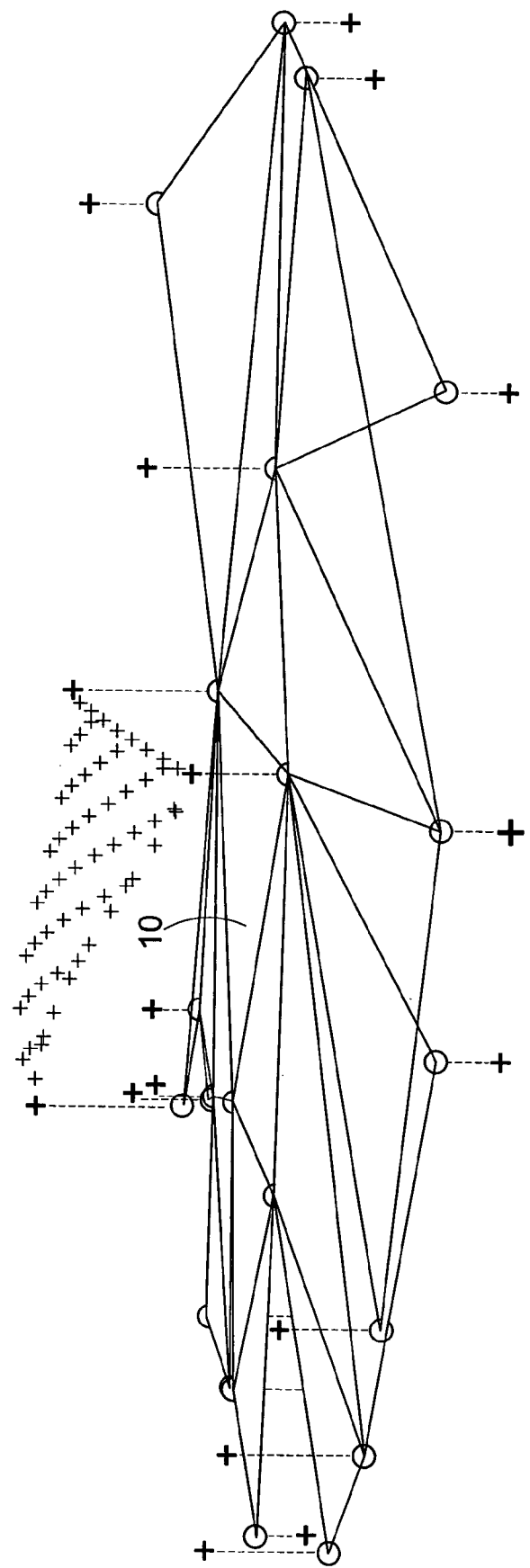
FIG. 9 shows sampling within the triangle of interest.

In a fifth stage, the bicubic spline interpolation is sampled within the triangle 10 of interest, as shown in FIG. 9. In order to ensure continuity, the samples may be adjusted using a weighted average of the bicubic splines obtained by unwrapping the points around each of the adjacent triangles 8.

In a sixth stage, the process described above in connection with FIGS. 5 to 9 is repeated for each triangle shown in FIG. 3. The data is then 're-wrapped' around the ellipse (reversing the process in FIG. 6), and joining all of the sampled points within the triangles results in a smooth mesh 14 which is in contrast to that obtained and shown in FIG. 4.

Figure 10:
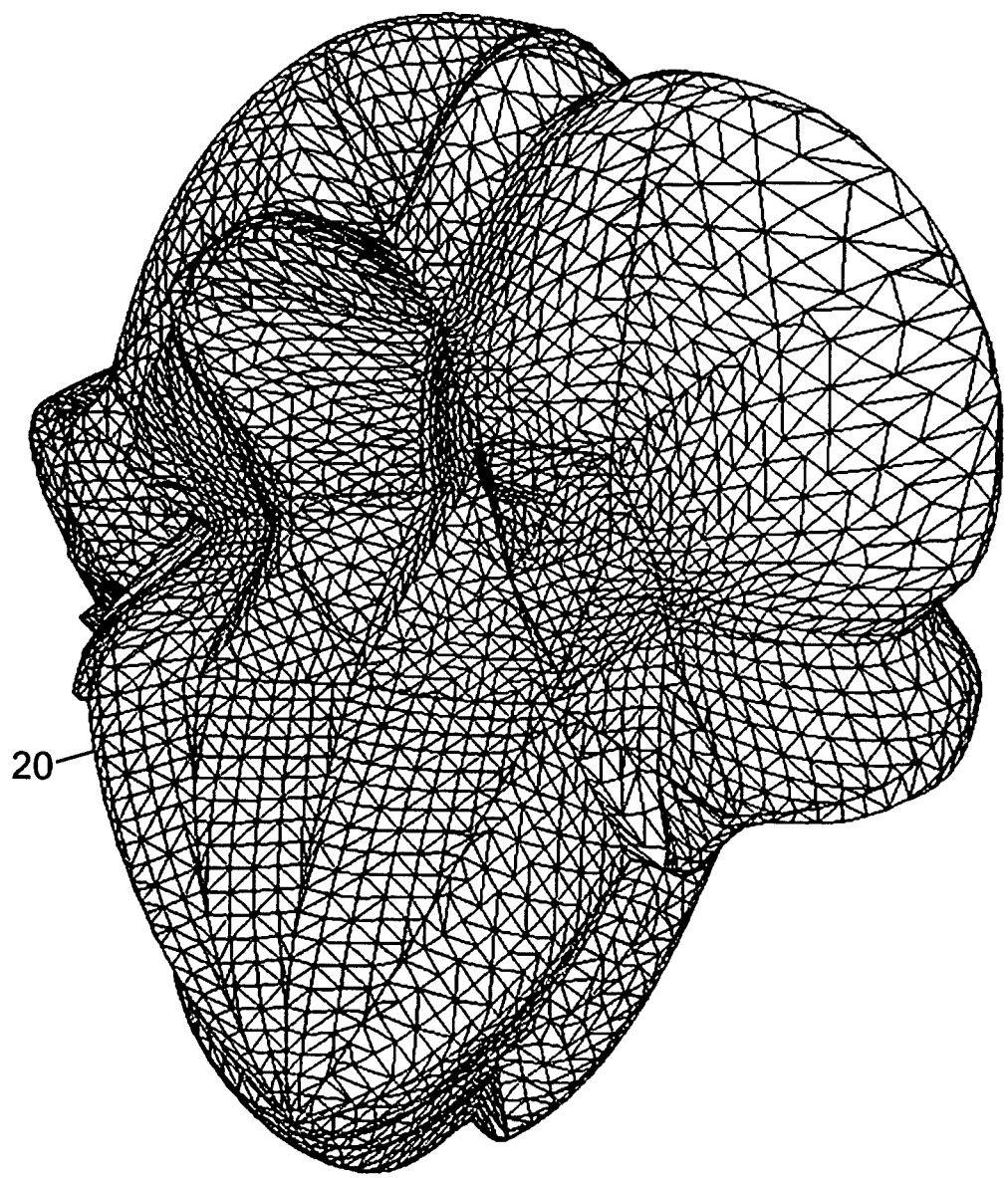
FIG. 10 is a graphical representation of the surface obtained after applying the process of FIGS. 5-9 to each triangle and wrapping the plane around the ellipse of FIG. 2 to obtain a smooth mesh, in accordance with a preferred embodiment of the present invention.
Figure 11:
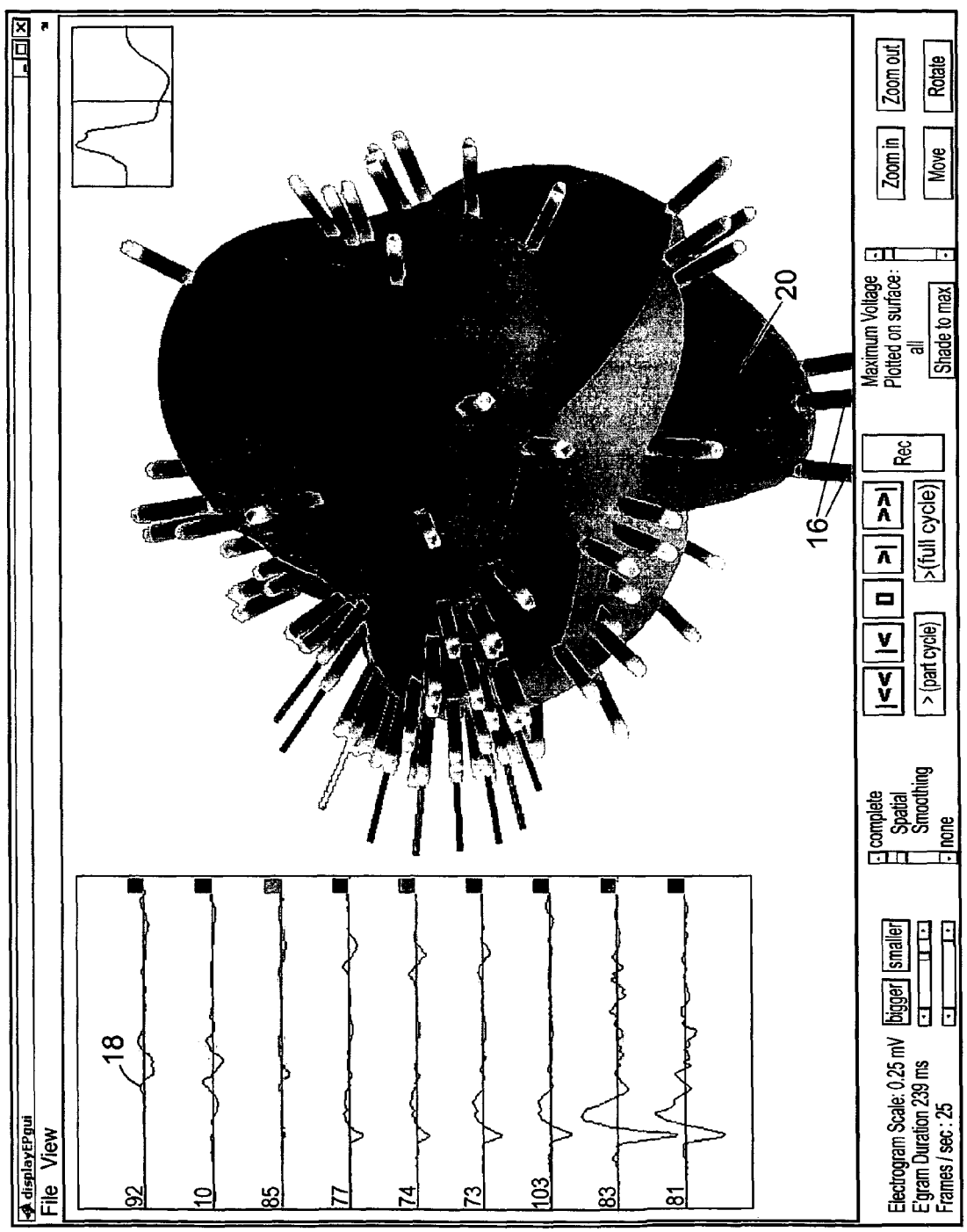
FIG. 11 is graphical representation of a heart of an individual generated using the process embodying the present invention in accordance with FIGS. 5 to 10 with electrogram bars positioned at each sampling point.

The next stage is to add electrogram data to the surface denoted by the smooth mesh 14 of FIG. 10. This is shown in FIG. 11. The electrograms are gated (or 'timed') relative to the surface ECG using standard algorithms. Alternatively, the electrograms may be gated to any other electrogram that is being measured as a reference, which may advantageously be an atrial electrogram. Each electrogram is displayed as a bar 16 that protrudes from the generated model 20 of the cardiac surface. The starting location is the position after spatial smoothing.

Preferably, the length of the bar 16 is related to the electrogram voltage. In the simplest embodiment, this representative length of the bars 16 may be linearly related to the actual voltage, but may have an alternative relationship. For example, any sequence of transformations drawn from the list below may be applied:

Absolute value: x:−>abs(x)

Logarithmic transformation: x:−>log(x+k) where k is some constant arranged that x+k is always >0

Square root: x:−>√x

Power relationship: x:−>x^n

Modified power relationship: x:−>(x")/(k+x")

Or any monotonic function

In each of the transformations shown above, "x" represents the voltage, and "k" and "n" are values which are kept constant for all the bars being displayed at any one time, but whose values may be changed by the operator if desired. These transformations are preferably arranged so as to make even small disturbances in voltage more apparent at voltages of interest (typically near the baseline).

The direction of the bar is preferably perpendicular to the convex hull nearest each point. This ensures that neighbouring electrograms are all slightly divergent and do not 'collide'.

Software controls allow the time within the cardiac cycle to be varied. For example, a 'movie' of the entire cardiac cycle may be created in which the electrogram bars 16 lengthen dynamically according to the voltage-time relationship at each point. A number of transformations may be applied to relate the length of the 'electrogram bar' 16 to the electrogram voltage, for example, various logarithmic transformations may advantageously be used.

if required, the electrogram from any point may be displayed on a standard voltage-time plot 18 on a display device such as a computer screen by selecting it with, for example, a connected computer mouse. Multiple electrograms may be displayed on the same axes by sequentially selecting the required points. This feature allows an extremely detailed analysis to be performed of pathways that have been identified on the 3D display.

In a preferred embodiment, a sterile hardware device may be made available to magnification to the operator to allow manipulation of the time that the electrograms are displayed within the cardiac cycle and also to allow the viewing angle and magnification to be altered. An example of such a device is a trackball or rotational knob.

In summary, one or more preferred embodiments of the present invention are particularly advantageous as they assist in the visualization of cardiac activation and substantially all of the information that has been acquired may be visualized to allow the user to visualize changing electrogram voltages across a 3D surface. Furthermore, the spatial positioning of points may be 'smoothed' to facilitate inspection of multiple electrogram signals at the same time. Derived variables may be interpolated around a reconstructed surface whilst viewing the original electrograms. Also, a human assistant is not required to routinely check the automated analysis or process any data before the data is displayed. In addition, the techniques embodying the invention may be used in conjunction with 3D cardiac location and recording systems.

Various modifications to the embodiments of the present invention described above may be made. For example, other components and method steps may be added or substituted for those above. In particular, instead of using the measured voltage obtained at given points, another parameter could equally well be interpolated across the reconstructed surface, for example, the maximum voltage of the electrogram. Also, visualization may be facilitated by colouring the surface according to the interpolation, or by causing the surface to move dynamically on the display screen. Furthermore, the surface and 'electrogram bars' may be rotated and manipulated in 3D to optimize the view of interesting areas. This may be achieved using standard algorithms and may be controlled by standard graphical user interface controls. The display of a continuous surface is helpful to visualizing the 'electrogram bars' but is not obligatory.

Also, in a preferred embodiment, an alternative method may be used to render the cardiac surface to which the electrogram bars may be applied. For example, reconstructed 3D CT (computed tomography) and reconstructed rotational angiography may be used.

Depending on the application in which the apparatus and methods embodying the invention are to be used, all or part of the apparatus/process steps described above may be constructed or integrated in hardware, or part or all of the apparatus/process steps described above may be implemented in software.

The invention claimed is:

1. A method of generating a model of a cardiac surface having a plurality of images representing electrogram voltages for a plurality of measured points within a heart comprising: internally measuring an electrogram voltage at a plurality of points within a heart; generating a first model of a cardiac surface of said heart; generating an image representing each electrogram voltage, each image having a characteristic representative of the electrogram voltage; and generating a further model of a cardiac surface, said images representing said electrogram voltages protruding from said further model of said cardiac surface at points on said further model corresponding to the points at which said electrogram voltages were measured.

2. A method according to claim 1, wherein the step of generating the first model of said cardiac surface comprises:
    (a) obtaining three-dimensional coordinates of the locations of said plurality of points at which said electrogram voltages were measured;
    (b) fitting a surface of a three-dimensional representation of a solid to said three-dimensional coordinates;
    (c) locating on the surface of said solid a plurality of points, one or more of said points corresponding to a respective one of said plurality of points at which said electrogram voltages were measured to generate associated surface points on said representation of said solid;
    (d) dividing said surface of said representation of said solid into a plurality of triangles, each triangle having an associated apex at which one of said plurality of said surface points is located;
    (e) transforming the surface of said three-dimensional representation of a solid into a two-dimensional plane around a first selected triangle of said plurality of triangles using a predetermined transformation process;
    (f) transforming the three-dimensional coordinates of the locations of the plurality of points at which said electrogram voltages were measured using said transformation process applied in step (e) to said surface;
    (g) connecting a number of said transformed points at which said electrogram voltages were measured to other of said transformed points at which said electrogram voltages were measured to form a further surface using a bicubic spline interpolation method;
    (h) sampling an area within said first selected triangle that was interpolated using the bicubic spline interpolation method, the samples being adjusted with a weighted average to obtain a shape representative of the surface of said triangle;
    (i) repeating steps (e), (f), (g) and (h) for each triangle of said plurality of triangles to obtain a plurality of three-dimensional surfaces representative of each of said plurality of triangles; and
    (j) transforming the three-dimensional surfaces into a three-dimensional model to form the first model of said cardiac surface.

3. A method according to claim 2, wherein said step of measuring an electrogram voltage at a plurality of points within a heart comprises measuring a maximum voltage for said plurality of said points and performing one or more of the steps (a) to (j) using said measured maximum voltage.

4. A method according to claim 2, further comprising applying one or more colours to said surface.

5. A method according to claim 2, wherein the step of fitting a three-dimensional representation of a solid comprises fitting the three-dimensional representation of said solid having a continuous surface to said measured points.

6. A method according to claim 2, wherein the step of fitting a solid comprises fitting a sphere to said three-dimensional coordinates.

7. A method according to claim 2, wherein the step of fitting a solid comprises fitting an ellipsoid to said three-dimensional coordinates.

8. A method according to claim 1, wherein the step of generating an image representing each electrogram voltage comprises generating a bar.

9. A method according to claim 8, wherein one or more of said bars have a length representative of the measured electrogram voltage.

10. A method according to claim 9, further comprising transforming the length of one or more of said bars to enhance visibility of small disturbances from baseline.

11. A method according to claim 10, wherein the step of transforming the length of one or more of said bars to enhance visibility of small disturbances from baseline comprises transforming using one or more of a series of transformations having one or more characteristics adjustable by a user.

12. A method according to claim 8, wherein one or more of said bars extend in a plane substantially perpendicular to said further model at the points of connection thereto.

13. A method according to claim 1, wherein said further model of said cardiac surface is movable.

14. A method according to claim 13, wherein said further model of said cardiac surface is rotatable.

15. A method according to claim 1, wherein said electrogram voltages are measured at a predetermined time in a cardiac cycle, the method further comprising varying the predetermined time within the cardiac cycle to obtain a revised representation on the further model at one or more further predetermined times within the cardiac cycle of the images representing each electrogram voltage at said one or more further predetermined times.

16. A method according to claim 1, further comprising altering one or more of a viewing angle of said further model, magnification of said further model, and/or the time at which the electrograms are displayed within a cardiac cycle.

17. A method according to claim 1, further comprising generating a movie of the images representing the electrogram voltages on the further model by displaying the images of electrogram voltages measured at various predetermined times during a cardiac cycle.

18. A method according to claim 1, wherein the step of generating the first model of said cardiac surface comprises: generating said first model using a reconstructed three-dimensional computed tomography (3D CT) process.

19. A method according to claim 1, wherein the step of generating the first model of said cardiac surface comprises: generating said first model using a reconstructed rotational angiography process.

20. A method according to claim 1, wherein the first model has a surface, the method further comprising smoothing the surface of the first model according to one or more user preferences.

21. An apparatus for generating a model of a cardiac surface having a plurality of images representing electrogram voltages for a plurality of measured points within a heart comprising: a first stage arranged to internally measure an electrogram voltage at a plurality of points within a heart; a second stage arranged to generate a first model of a cardiac surface of said heart; a third stage arranged to generate an image representing each electrogram voltage, each image having a characteristic representative of the electrogram voltage; and a fourth stage arranged to generate a further model of a cardiac surface, said images representing said electrogram voltages protruding from said further model of said cardiac surface at points on said further model corresponding to the points at which said electrogram voltages were measured.

22. An apparatus according to claim 21, wherein the second stage comprises:
 (a) a three-dimensional coordinate determination stage to determine the three-dimensional coordinates of the locations of said plurality of points at which said electrogram voltages were measured;
 (b) a fitting stage to fit a surface of a three-dimensional representation of a solid to said three-dimensional coordinates;
 (c) a location stage to locate on the surface of said solid a plurality of points, one or more of said points corresponding to a respective one of said plurality of points at which said electrogram voltages were measured to generate associated surface points on said representation of said solid;
 (d) a divider stage to divide said surface of said representation of said solid into a plurality of triangles, each triangle having an associated apex at which one of said plurality of said surface points is located;
 (e) a first transformation stage arranged to transform the surface of said three-dimensional representation of a solid into a two-dimensional plane around a first selected triangle of said plurality of triangles using a predetermined transformation process;
 (f) a second transformation stage arranged to transform the three- dimensional coordinates of the locations of the plurality of points at which said electrogram voltages were measured using said transformation process applied to said surface;
 (g) a connecting stage to connect a number of said transformed points at which said electrogram voltages were measured to other of said transformed points at which said electrogram voltages were measured to form a further surface using a bicubic spline interpolation method;
 (h) a sampling stage to sample an area within said first selected triangle that was interpolated using the bicubic spline interpolation method, the samples being adjusted with a weighted average to obtain a shape representative of the surface of said triangle;
 (i) said first and second transformation stages, said connecting stage and said sampling stage being arranged to operate on each triangle of said plurality of triangles to obtain a plurality of three-dimensional surfaces representative of each of said plurality of triangles; and
 (j) a third transformation stage arranged to transform the three-dimensional surfaces into a three-dimensional model to form the first model of said cardiac surface.

23. An apparatus according to claim 22, wherein said first stage is arranged to measure a maximum electrogram voltage for said plurality of said points, wherein one or more of said three-dimensional coordinate determination stage, said fitting stage, said location stage, said divider stage, said first transformation stage, said second transformation stage, said connecting stage, and said sampling stage being arranged to operate using said measured maximum voltages.

24. An apparatus according to claim 22, wherein said surface has one or more colours applied to said surface.

25. An apparatus according to claim 22, wherein said fitting stage is arranged to fit the three-dimensional representation of said solid having a continuous surface to said measured points.

26. An apparatus according to claim 22, wherein the fitting stage is arranged to fit a sphere to said three-dimensional coordinates.

27. An apparatus according to claim 22, wherein the fitting stage is arranged to fit an ellipsoid to said three-dimensional coordinates.

28. An apparatus according to claim 21, wherein said image representing each electrogram voltage comprises a bar.

29. An apparatus according to claim 28, wherein one or more of said bars have a length representative of the measured electrogram voltage.

30. An apparatus according to claim 29, further comprising a transformation stage arranged to transform the length of one or more of said bars to enhance visibility of small disturbances from baseline.

31. An apparatus according to claim 30, wherein the transformation stage is arranged to transform the length of one or more of said bars to enhance visibility of small disturbances from baseline by one or more of a series of transformations having one or more characteristics adjustable by a user.

32. An apparatus according to claim 28, wherein one or more of said bars extend in a plane substantially perpendicular to said further model at the points of connection thereto.

33. An apparatus according to claim 21, wherein said further model of said cardiac surface is movable.

34. An apparatus according to claim 33, wherein said further model of said cardiac surface is rotatable.

35. An apparatus according to claim 21, wherein said electrogram voltages are measured at a predetermined time in a cardiac cycle, the apparatus further comprising varying the predetermined time within the cardiac cycle to obtain a revised representation on the further model at one or more further predetermined times within the cardiac cycle of the images representing each electrogram voltage at said one or more further predetermined times.

36. An apparatus according to claim 21, further comprising a stage for altering one or more of a viewing angle of said further model, magnification of said further model, and/or the time at which the electrograms are displayed within a cardiac cycle.

37. An apparatus according to claim 21, further comprising a stage arranged to generate a movie of the images representing the electrogram voltages on the further model by displaying the images of electrogram voltages measured at various predetermined times during a cardiac cycle.

38. An apparatus according to claim 21, wherein the second stage is arranged to generate the first model of said cardiac surface using a reconstructed three-dimensional computed tomography (3D CT) process.

39. An apparatus according to claim 21, wherein the second stage is arranged to generate the first model of said cardiac surface using a reconstructed rotational angiography process.

40. An apparatus according to claim 21, wherein the first model has a surface, the apparatus further comprising a smoothing stage arranged to smooth the surface of the first model according to one or more user preferences.

* * * * *